US008834851B2

(12) United States Patent
Haeberlein et al.

(10) Patent No.: US 8,834,851 B2
(45) Date of Patent: Sep. 16, 2014

(54) DENTAL COMPOSITION FOR DETECTING BACTERIA, KIT OF PARTS AND USE THEREOF

(75) Inventors: Ingo R. Haeberlein, Weilheim (DE); Melanie Hauke, Wörthsee (DE); Oliver Kappler, Weilheim (DE); Thomas Luchterhandt, Greifenberg (DE); Adelheid Stöger, Peiting (DE)

(73) Assignee: 3M Innovative Properties Company, St. Paul, MN (US)

( * ) Notice: Subject to any disclaimer, the term of this patent is extended or adjusted under 35 U.S.C. 154(b) by 431 days.

(21) Appl. No.: 12/677,377

(22) PCT Filed: Oct. 23, 2008

(86) PCT No.: PCT/US2008/080886
§ 371 (c)(1),
(2), (4) Date: Mar. 10, 2010

(87) PCT Pub. No.: WO2009/055530
PCT Pub. Date: Apr. 30, 2009

(65) Prior Publication Data
US 2011/0008748 A1   Jan. 13, 2011

(30) Foreign Application Priority Data

Oct. 26, 2007 (EP) .................................... 07119353
Jul. 17, 2008 (EP) .................................... 08160597

(51) Int. Cl.
| A61K 8/18 | (2006.01) |
| C12Q 1/04 | (2006.01) |
| A61K 6/00 | (2006.01) |

(52) U.S. Cl.
CPC .. *A61K 6/002* (2013.01); *C12Q 1/04* (2013.01)
USPC .......................................................... 424/49

(58) Field of Classification Search
USPC ....................................................... 424/94.4
See application file for complete search history.

(56) References Cited

U.S. PATENT DOCUMENTS

| 3,332,743 | A | 7/1967 | Green |
| 4,254,222 | A | 3/1981 | Owen |
| 4,351,899 | A | 9/1982 | Owen |
| 4,359,455 | A | 11/1982 | Nakamura et al. |
| 4,582,795 | A | 4/1986 | Shibuya et al. |
| 6,105,761 | A | 8/2000 | Peuker et al. |
| 7,097,075 | B2 | 8/2006 | Peuker et al. |
| 7,175,430 | B1 | 2/2007 | Gasser et al. |
| 2004/0141960 | A1 | 7/2004 | Haberlein et al. |

FOREIGN PATENT DOCUMENTS

| DE | 101 08 900 | | 3/2005 | |
| JP | 2004-113129 | * | 4/2004 | ............... C12Q 1/32 |
| WO | WO 98/33936 | | 8/1998 | |
| WO | WO 00/24438 | | 5/2000 | |
| WO | WO 01/12237 | | 2/2001 | |

OTHER PUBLICATIONS

Cesari et al., Localization and Properties of Enzymes Involved with Electron Transport Activity in Mycobacteria, J. of Bacteriology, 1969, 98(2), pp. 767-773.*
Mills, Occurrence of Mycobacterium Other than Mycobacterium tuberculosis in the Oral Caivty and in Sputum, Applied Microbiol., 1972, 24(3), pp. 307-310.*
International Search Report PCT/US2008/080886 Aug. 9, 2009; 4 pgs.
Schweikl and Schmalz in Eur J Oral Science 1996: 104:292-299 "Toxicity parameters for cytotoxicity testing of dental materials in two different mammalian cell lines".
Freimoser et al. in Applied and Environmental Microbiology 1999 Aug. 65(8):3727-3729 "The MTT-Assay is a fast and reliable method for colorimetric determination of fungal cell densities".
Ansari, Beeley, Reid and Foye in Journal of Oral Rehabilitation, "Caries Detector Dyes—An In Vitro Assessment of Some New Compounds"; 1999, 26; 453-458.
Veiga-Malta et al; Journal of Bacteriology, Jan. 2004, p. 419-426, "Identification of NAD* Synthetase from *Streptococcus sobrinus* as a B-Cell-Stimulatory Protein".

* cited by examiner

*Primary Examiner* — Brian Gulledge
(74) *Attorney, Agent, or Firm* — Nicole J. Einerson

(57) ABSTRACT

The invention relates to a dental composition for detecting bacteria comprising a solvent, at least one electron acceptor component and at least one electron donor component, the composition being substantially free of components which enable or facilitate the electron transmission between the electron acceptor component and the electron donor component. The invention also relates to a kit of parts and the use of the dental composition for producing a means for the interoral detection of bacteria.

20 Claims, No Drawings

DENTAL COMPOSITION FOR DETECTING BACTERIA, KIT OF PARTS AND USE THEREOF

CROSS-REFERENCE TO RELATED APPLICATIONS

This is a national stage filing under 35 U.S.C. 371 of PCT/US2008/080886 filed Oct. 23, 2008, which claims priority to European Patent Application No. 07119353.6, filed Oct. 26, 2007 and European Patent Application No. 08160597.4, filed Jul. 17, 2008, the disclosures of which are incorporated by reference in their entirety herein.

FIELD OF THE INVENTION

The present invention relates to a dental composition. It more specifically relates to the use of a composition for intra-oral site-directed detection of bacteria. It further relates to a method of intra-oral site-directed detection of bacteria.

BACKGROUND

Oral bacteria colonize hard and soft tissues in mouth such as gums, tongue, enamel, dentin, root cement and dental restorations. Oral bacteria residing on enamel, dentin, cement and dental restorations supra- and sub-gingival can cause demineralisation of the hard tissue and destruction of the periodontium.

Different technologies are available for detecting caries lesions. Most of these techniques involve detecting sites of demineralization that are associated with caries lesions. These technologies generally involve analyzing the degree of demineralization though any of a variety of techniques, including the use of visual and tactile methods, X-rays and electro-chemical methods, and the use of certain dyes. The degree of observable demineralization determines how advanced the caries process has already damaged a tooth.

In general, technologies for detecting caries via detecting demineralization are not able to differentiate between infected and affected tooth tissue, which can lead to over-excavation of caries lesions. Affected tooth tissues, representing non-infected but partially demineralised hard tooth tissue, is found below the layer of infected hard tooth tissue. Infected hard tooth tissue should be removed but affected hard tooth tissue should be saved for remineralisation. For example, Ansari, Beeley, Reid and Foye (Journal of Oral Rehabilitation, 1999, 26; 453-458) determined that common dyes are not caries specific because they stain demineralized organic matrix and therefore cannot differentiate between infected non-remineralizable tissue and reversibly decalcified tissue.

Moreover, all procedures which detect caries via the degree of demineralization cannot immediately indicate if the caries process is still active or arrested. To differentiate between active and arrested caries lesions a second investigation, mostly many months later, is required to observe ongoing mineral loss over time.

Demineralization of hard tooth tissue is caused by the action of caries bacteria colonizing hard tooth tissues in mouth. All procedures which detect caries via the degree of demineralization have to wait until the caries bacteria have caused a detectable degree of mineral loss. In contrast, a procedure that is able to detect the deleterious action of caries bacteria on teeth before demineralization becomes detectable would have the advantage of being able to prevent initial caries even in its earliest stage.

U.S. Pat. No. 3,332,743 describes a test solution for evaluating individual's dental caries risk in measuring the color change of diazoresorcinol in saliva samples. However, this procedure does not provide any information about the location of caries bacteria on tooth surfaces.

In other procedures, plaque collected from tooth surfaces is used to evaluate the inherent activity to metabolize, glucose, saccharose or other sugars into organic acids outside the mouth. In one aspect, acid formation is followed by pH change occurring over time by pH indicators (U.S. Pat. No. 4,359,455). In another aspect, the lactic acid formation in the plaque sample is evaluated by the use of enzymes (i.e. lactate dehydrogenase), whereby the enzymatic reaction is linked to redox dyes to generate a visual signal (DE 10108900). Although it is well-known that the caries activity in plaque differs significantly from site to site on teeth, both procedures mix plaque from several tooth surfaces to evaluate acid production in response to the presence of carbohydrates.

DE 101 08 900 (corresponding to US 2004/0141960) relates to a process for the determination of individual's caries risk in presence of carbohydrates in saliva or plaque samples. Lactate dehydrogenase, Pyruvat, sucrose and oxidized nicotinamide adenine dinucleotide (NAD) are added and the formation of reduced nicotinamide adenine dinucleotide (NADH) is detected e.g. by redox indicators like MTT using an electron carrier, i.e. PMS.

U.S. Pat. No. 4,351,899 and U.S. Pat. No. 4,254,222 refers to procedures for measuring lactic acid in biological fluids. Lactate dehydrogenase, NAD, an electron carrier and a tetrazolium dye as redox indicator is used to measure lactic acid. In case the biological fluid is saliva, an intra-oral site directed detection of caries bacteria residing on teeth/tooth surfaces is not possible.

JP 2004-113129 shows a liquid for specifying lactic acid producing region surrounding tooth surface, comprises preset amount of lactate dehydrogenase, oxidized nicotinamide adenine dinucleotide, electronic-transition agent, tetrazolium salt and water EP 1 191 946 relates to a procedure for intra-oral directed detection of caries bacteria residing on teeth/tooth surfaces which is based on a dental impression material supplemented with lactate dehydrogenase, oxidized nicotinamide adenine dinucleotid, a redox dye, e.g. MTT and an electron carrier, e.g. PMS.

The [3-(4,5-dimethylthiazol-2-yl)-2,5-diphenyltetrazolium bromide]-assay (MTT-Assay) is widely known as a test for the detection of living cells. With different modifications and adjustments the test includes an incubation of cells with MTT in an aqueous solution for usually 4 to 8 hours. E.g. Schweikl and Schmalz used it to determine the "Toxicity parameters for cytotoxicity testing of dental materials in two different mammalian cell lines" (Eur J Oral Sci. 1996 June; 104(3):292-9.).

Freimoser et al. published in "The MTT-Assay Is a Fast and Reliable Method for Colorimetric Determination of Fungal Cell Densities" (Applied And Environmental Microbiology 1999 August; 65(8): 3727-3729) the use of the MTT-Assay as a colorimetric method for the determination of cell densities. The samples containing the cells to be detected are incubated for 16 hours.

SUMMARY OF THE INVENTION

It would therefore be desirable to provide a composition, its use and a method for quick and reliable detection of the presence of bacteria in the mouth, on hard tooth tissue (enamel, root cement and dentin) and on dental restorations.

It would further be desirable to provide a composition and a method for intra-oral site-directed detection of bacteria.

In one aspect, the invention relates to a bacteria detecting dental composition comprising a solution of at least one electron acceptor and at least one electron donor. The electron acceptor and the electron donor are selected such that in the solution itself the electron donor does not transmit reduction equivalents to the electron acceptor. Further, the dental composition is substantially free of compounds that enable or facilitate the electron transmission between the electron acceptor and the electron donor.

Another aspect of the invention features the use of a composition as described the text of the invention for producing a means for the intra-oral detection of bacteria.

DEFINITIONS

A "composition" is understood to be a mixture of two or more components.

The term "water-soluble" means that a substance as such is soluble in water at ambient conditions, comparable to a salt. That is, the substance is able to form individual molecules in water like glucose when dispersed in water at 23° C.

A "particle" means a substance being a solid having a shape which can be geometrically determined. Particles can typically be analysed with respect to e.g. grain size.

A "dental compositions and dental articles" is a composition which is to be used in the dental field (including restorative and prosthodontic work) including the orthodontic area. In this respect the composition should be not detrimental to the patient's health and thus free of hazardous and toxic components being able to migrate out of the composition. Commercially available products have to fulfil certain requirements such as those given in DIN EN 21942-2.

A substance is classified as "liquid or solvent" if it has a viscosity below about 100 Pa*s or below about 50 Pa*s or below about 5 Pa*s at 25° C.

The term "essentially/substantially free of a substance" is to be understood that a certain substance is typically not present at all or has not been wilfully added. However, it might happen that sometimes unavoidable traces of this substance can be detected.

Thus, "essentially free of component X" means that the content of component X (especially added component X) in a composition is less than about 5 wt.-% or less than about 2 wt.-% or less than about 1 wt.-% or less than about 0.1 wt.-% with respect to the whole composition.

The term "visible light" is used to refer to light having a wavelength of about 400 to about 1000 nanometers (nm).

"Reduction potential" (also known as redox potential, oxidation/reduction potential) is the tendency of a chemical species to acquire electrons and thereby be reduced. Each species has its own intrinsic reduction potential; the more positive the potential, the greater the species' affinity for electrons and tendency to be reduced.

In aqueous solutions, the reduction potential is the tendency of the solution to either gain or lose electrons when it is subject to change by introduction of a new species. A solution with a higher (more positive) reduction potential than the new species will have a tendency to gain electrons from the new species (i.e. to be reduced by oxidizing the new species) and a solution with a lower (more negative) reduction potential will have a tendency to lose electrons to the new species (i.e. to be oxidized by reducing the new species). Just as the transfer of hydrogen ions between chemical species determines the pH of an aqueous solution, the transfer of electrons between chemical species determines the reduction potential of an aqueous solution.

The reduction potential is typically measured in volts (V) or millivolts (mV). Because the absolute potentials are sometimes difficult to accurately measure, reduction potentials are often defined relative to a standard hydrogen electrode which is arbitrarily given a potential of 0.00 volts. Standard reduction potential (E0), is measured under standard conditions: 25° C., a 1 M concentration for each ion participating in the reaction, a partial pressure of 1 atm for each gas that is part of the reaction, and metals in their pure state.

Nicotinamide adenine dinucleotide, abbreviated $NAD^+$, is a coenzyme which can be found in living cells. The compound is a dinucleotide, since it consists of two nucleotides joined through their phosphate groups: with one nucleotide containing an adenosine ring, and the other containing nicotinamide.

In metabolism, $NAD^+$ is typically involved in redox reactions, carrying electrons from one reaction to another. $NAD^+$ is an oxidizing agent—it accepts electrons from other molecules and becomes reduced, this reaction forms NADH, which can then be used as a reducing agent to donate electrons. These electron transfer reactions are the main function of $NAD^+$.

An "electron donor" or "electron donor component" is a chemical entity that can donate electrons to another component. It is a reducing agent that, by virtue of its donating electrons, is itself oxidized in the process.

An "electron acceptor" or "electron acceptor component" is a chemical entity that accepts electrons transferred to it from another compound. It is an oxidizing agent that, by virtue of its accepting electrons, is itself reduced in the process.

The term "intra-oral" means that the inventive composition is applied in the mouth of a patient without the need for conducting additional steps outside the intra-oral area, e.g. in a laboratory.

The term "site-directed" means that a signal is generated which indicates where residual infected dentin is located in a caries infected cavity. This allows for site directed localisation of residual infected dentin in a caries infected cavity. A site directed signal indicates the sites which typically require further treatment.

A "derivative" is a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

"Ambient conditions" mean the conditions which the inventive composition is usually subjected to during storage and/or handling. Ambient conditions may, for example, be a pressure of about 900 to about 1100 mbar, a temperature of about −10 to about 60° C. and a relative humidity of about 10 to about 100%. In the laboratory ambient conditions are typically adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF THE INVENTION

It is one aspect of the present invention that the electron acceptor component and the electron donor component are selected that they can not react together in the solution. After applying the solution containing electron acceptor and electron donor to different sites of the oral cavity the electron acceptor becomes reduced due to the presence of bacteria.

Without wishing to be bound to a particular theory, it is assumed that the bacteria contain a kind of electron carrier that may facilitate the electron transmittal from the electron donor component to the electron acceptor component in the invented dental composition. Then, the reduction of the electron acceptor component occurs by transfer of one or more electrons provided by the electron donor component when the invented dental composition gets in contact with bacteria.

The electron acceptor and/or the electron donor components are typically selected such that they have different colors in their reduced and in their oxidized state. For example, at least in its reduced state the electron acceptor component shows a color in the visible range of about 380 nm to about 780 nm wave length. Thus, it is possible that the dental practitioner notices visually the color change of the electron acceptor component between its oxidized and its reduced state in the composition.

There are different possibilities for this change.

On the one hand the composition is colorless before applied to different intra-oral sites. Reduction of the electron acceptor component causes a color change visibly by the human eye. On the other hand it could change that way, that the composition has a distinctive color before its application. If the electron acceptor component is reduced the color can change to one showing a color which is visibly by eye and clearly distinctive from the color of the electron acceptor in the oxidized state.

In another embodiment of the present invention the electron acceptor component in its reduced state emits fluorescence light in the visible wavelength range of about 380 nm to about 780 nm, which gives the electron acceptor component in its reduced state a self-shining characteristic.

It is further possible for another embodiment of the present invention that the electron donor component is selected such that it has different colors in its oxidized and in its reduced state. For example, the electron donor component in its oxidized state shows a color in the visible range of about 380 nm to about 780 nm wave length. Thus, it is possible that the dental practitioner notices visually the color change of the electron donor component between its reduced and its oxidized state in the composition.

The electron acceptor component and the electron donor component may be present each in a concentration that allows to pursue the color change with the human eye.

In one preferred embodiment, the electron donor component is present in a concentration of about 0.5 to about 13 mg/ml or of about 1.0 to about 3.5 mg/ml with respect to the total composition. In case the electron donor is one of the NADH- or NADPH-analogues as described in WO 98/33936, the concentration can be in a range of about 10.0 to about 13.0 mg/ml or about 9 mg/ml to about 12 mg/ml with respect to the total composition.

The electron acceptor component may be present in a concentration of about 1.0 to about 3.5 mg/ml or in a concentration of about 1.5 to about 2.5 mg/ml with respect to the total composition.

The solubility of the electron donor component and the electron acceptor component in the composition respectively the solvent of the inventive dental composition has to be that high that the intra-oral site-directed detection of bacteria is possible. That means that the concentration of the solved electron acceptor and the solved electron donor has to be as high as a distinctive color is perceivable.

The electron donor component and/or the electron acceptor component can be present in the composition in an amount from about 0.01 wt.-% to about 80 wt.-% or about 0.05 wt.-% to about 30 wt.-% with respect to the total weight of the composition. It can be advantageous if the electron acceptor component and the electron donor component is present in the composition in an amount from about 0.01 to about 10 wt.-% with respect to the total weight of the composition.

Preferably the electron acceptor component shows different solubility in its oxidized and in its reduced state in the respective solvent. That is, when the electron acceptor component gets reduced its solubility will be lowered that far that the electron acceptor component in its reduced form precipitates at the site where the electron acceptor component gets reduced, which allows intra-oral site directed detection of bacteria. In another embodiment the electron donor component shows a lower solubility in its oxidized state in the respective solvent. Even here the solubility should diminish as much as a precipitation occurs at the site where the electron donor component gets oxidized.

Of course there are other ways to make the detection of bacteria site-directed e.g. if the composition shows a high viscosity or forms a film.

In one embodiment, the electron acceptor component according to the present invention is a tetrazolium compound, a tetrazolium derivative or comprises a tetrazolium moiety.

This tetrazolium compound or tetrazolium derivate can be selected e.g. from the group containing 2-(2'-benzothiazolyl)-5-styryl-3-(4'-phthalhydrazidyl)tetrazolium chloride, 2-(2-benzothiaolyl)-3-(4-nitrophenyl)-5-phenyltetrazolium bromide, 2-(2-benzothiaolyl)-3,5-diphenyltetrazolium bromide, 2-(4-iodophenyl)-3-(4-nitrophenyl)-5-phenyl-2H-tetrazolium chloride, 2-(4-iodophenyl)-3-(4-nitrophenyl)-5-phenyltetrazolium chloride, 2-(4-iodophenyl)-3-(4-nitrophenyl)-5-phenyltetrazolium chloride hydrate, 2,3,5-triphenyl-2H-tetrazolium chloride, 2,3,5- triphenyltetrazolium bromide, 2,3,5-triphenyltetrazolium chloride, 2,3,5-triphenyltetrazolium iodide, 2,3,5-tris(p-tolyl)tetrazolium chloride, 2,3-bis(3-chlorophenyl)-5-phenyltetrazolium chloride, 2,3-bis(3-fluorophenyl)-5-phenyltetrazolium chloride, 2,3-bis(3-methylphenyl)-5-phenyltetrazolium chloride, 2,3-bis(4-chlorophenyl)-5-phenyltetrazolium chloride, 2,3-bis(4-ethylphenyl)-5-phenyltetrazolium chloride, 2,3-bis(4-fluorophenyl)-5-phenyltetrazolium chloride, 2,3-bis(4-methoxyphenyl)-5-(4-cyanophenyl)tetrazolium chloride, 2,3-bis(4-methoxyphenyl)-5-phenyltetrazolium chloride, 2,3-bis(4-methylphenyl)-5-(4-cyanophenyl)tetrazolium chloride, 2,3-bis(4-nitrophenyl)-5-phenyltetrazolium chloride, 2,3-bis(4-nitrophenyl)-5-phenyltetrazolium chloride hydrate, 2,3-di(p-tolyl)-5-phenyltetrazolium chloride, 2,3-diphenyl-5-(2-thienyl)tetrazolium chloride, 2,3-diphenyl-5-(4-chlorophenyl)tetrazolium chloride, 2,3-diphenyl-5-(4-methoxyphenyl)tetrazolium chloride, 2,3-diphenyl-5-(p-diphenyl)tetrazolium chloride, 2,3-diphenyl-5-(p-tolyl)tetrazolium chloride, 2,3-diphenyl-5-aminotetrazolium chloride, 2,3-diphenyl-5-carboxytetrazolium chloride, 2,3-diphenyl-5-ethyltetrazolium chloride, 2,3-diphenyl-5-methyltetrazolium chloride, 2,5-di(p-tolyl)-3-phenyltetrazolium chloride, 2,5-diphenyl-3-(2,6-dimethylpheny)tetrazolium chloride, 2,5-diphenyl-3-(4-styrylphenyl)tetrazolium chloride, 2,5-diphenyl-3-(p-dipheny)tetrazolium chloride, 2-benzothiazolyl-3-(4-carboxy-2-methoxyphenyl-(5-[4-(2-sulfoethylcarbamoyl)phenyl]-2H-tetrazolium, 2-phenyl-3-(4-biphenylyl)-5-methyltetrazolium chloride, 2-phenyl-3-(4-carboxyphenyl)-5-methyltetrazolium chloride, 3-(3-nitrophenyl)-5-methyl-2-phenyltetrazolium chloride, 3-(4,5-dimethyl)-2-thiazolyl(-2,5-diphenyl-2H)-tetrazolium bromide, 3-(4,5-dimethyl)-2-thiazolyl(-2,5-diphenyl-2H)-tetrazolium chloride, 3-(4,5-dimethyl-2-thiazolyl)-2,5-diphenyltetrazolium bromide, 3-(4-nitrophenyl)-5-methyl-2-phenyltetrazolium chloride, 3,3'-(3,3'-dimethoxy-4,4'-diphenylene)bis(2-phenyl-5-veratryltetrazolium chloride), 3,3'-(3,3'-dimethoxy-4,4'-diphenylene)bis[2-(3-nitrophenyl)-5-phenyl]-2H-tetrazolium chloride, 4-[3-(4-iodophenyl)-2-(2,4-dinitrophenyl)-2H-5-tetrazolio]-1,3-benzene disulfonate, 4-[3-(4-iodophenyl)-2-(4-nitrophenyl)-2H-5-tetrazolio]-1,3-benzene disulfonate, 5-cyano-2,3-di-(p-tolyl)tetrazolium chloride, tetrazolium Blue chloride (Blue tetrazolium), cinnamyl nitro Blue tetrazolium chloride, Iodonitrotetrazolium chloride, m-tolyltetrazolium Red, Neotetrazolium chloride diformazan, Nitro Blue Tetrazolium, Nitro Blue Tetrazolium monohydrate, Nitro Neotetrazolium chloride (Violet), o-tolyltetrazolium Red, p-anisyl Blue tetrazolium chloride, p-anisyl Blue tetrazolium chloride diformazan, piperonyl tetrazolium Blue, p-tolyltetrazolium Red, tetranitro Blue Tetrazolium, 2,5-diphenyl-3-(1-naphthyl)tetrazolium chloride (tetrazolium Violet), 2,2'-bipheny-4,4'-dihylbis-(3,5-diphenyl-2H-terazolium)-dichlorid (Tetrazolpurpur), thiocarbamyl nitro Blue tetrazolium chloride, veratryl tetrazolium Blue. Mixtures and combinations thereof are also included.

Especially preferred electron acceptors include 2,3,5-triphenyltetrazolium bromide, 2,3,5-triphenyltetrazolium chloride, 2,3,5-triphenyltetrazolium iodide, 3-(4,5-Dimethyl)-2-thiazolyl(-2,5-diphenyl-2H)-tetrazolium bromide, Tetrazolium Violet/2,5-diphenyl-3-(1-naphthyl)tetrazolium chloride and/or Tetrazolpurpur/2,2'-bipheny-4,4'-dihylbis-(3,5-diphenyl-2H-terazolium)-dichloride and mixtures or combinations thereof.

A particularly useful electron acceptor component which can be used in the present invention is 3-(4,5-dimethylthiazol-2-yl)-2,5-diphenyltetrazolium-bromide (MTT).

Using MTT for measuring or detecting cellular growth is known in the art. However, as shown in the examples below, using a solution containing MTT as electron acceptor component only is not practicable in the dental field because the reaction typically requires a comparable long time (e.g. up to about 5 min) until a colour change can be observed. Surprisingly it has been found that adding an electron donor component like NADH to a composition containing an electron acceptor component enhances the reaction.

Even more surprisingly this reaction occurs within a comparable short time period absent of components which enable or facilitate the electron transmission between the electron acceptor and the electron donor like PMS, components which are usually needed for supporting the electron transfer.

Without wishing to be bound to a certain theory, it is believed that bacteria being present in the oral cavity of a living animal or human being contain components or structures which may function as an electron transfer supporting element.

Thus, in contrast to compositions containing MTT known from the state of the art, the inventive composition contains at least one electron donor component. This electron donor component can be selected from the group containing reduced nicotinamide adenine dinucleotide, reduced nicotinamide adenine dinucleotidephosphate, reduced flavine adenine dinucleotide, reduced flavine mononucleotide (riboflavine-5'-phosphate) and mixtures or combinations thereof. Further possible is the use of a derivative of said donors or the use of NADPH and NADH analogues according to WO 98/33936 which is incorporated herein by reference and of mixtures of two or more donors of this group.

After exposing the inventive composition to bacteria the reaction starts. It has been observed that the transmittal of reduction equivalents and the above mentioned color change of the inventive composition typically occurs in about 4 minutes or less, preferably in less than about 2 minutes, more preferably in less than about 1 minute, even more preferably in less than about 30 seconds and most preferably in about 20 seconds or less.

If the color change occurs later than about 4 minutes, the composition is likely to be not appropriate for dental purposes as the dental practitioner and/or the patient will typically not wait for more than about 4 minutes for a possible color change. In the dental practice it usually beneficial if procedures are fast because the patient and/or the dental practitioner try to reduce waiting times as far as possible, e.g. in order to save costs and/or to make the situation more convenient for the patient and the dental practitioner. In contrast to the state of the art compositions requiring typically an incubation period of about 4 to about 16 hours before the change of color can be measured or becomes visible to the human eye, the inventive composition requires far less time.

As the inventive composition is a solution, it contains a solvent. Typical solvents which can be used include water and organic solvents including alcohols (e.g. methyl alcohol, ethyl alcohol, n- and iso-propyl) alcohol and ketons (e.g acetone) and combinations thereof. If the solvent is or contains water, an aqueous solution containing the electron acceptor and the electron donor is typically formed.

In the case of a mixture of one or more organic solvents with water the concentration of the organic solvents can be from about 0.1 wt.-% to about 60 wt.-% related to the total solution. Typically, water is the preferred solvent. One or more organic solvents may be added e.g. in order to adjust the solubility of the electron acceptor in its oxidized state and the electron donor in its reduced state in the solution or to improve the wettability of the area in the mouth the composition is to be applied to.

Suitable organic solvents include for example linear, branched or cyclic, saturated or unsaturated alcohols with about 2 to about 10 C atoms, ketones as e.g. dialkyl ketones, esters, carboxylic acids, polymerizable substances of low viscosity such as polyethylene glycol (PEG), hydroxyethyl methacrylate or (2,3-epoxypropyl)methacrylate and mixtures of two or more of said types of solvents. Preferred solvents include water and water-alcohol mixtures.

Especially preferred alcoholic solvents are methanol, ethanol, iso-propanol and n-propanol.

Other suitable organic solvents are glycerin, dimethyl sulfoxide, tetrahydro furane, acetone, methyethyl ketone, cyclohexanol, toluene, methylen chloride, chloroform, alkanes and acetic acid alkyl esters, in particular acetic acid ethyl ester.

The pH value of the composition can be varied in a wide range. For example it is possible that the pH value is from about 1 to about 12. More preferred is a pH value of the composition from about 7 to about 10. If a two component system is used, the one component can have a pH value of about 10 to about 12 and the other component can have a pH value of about 1.5 to about 4. The pH value chosen should provide a condition where the electron acceptor and the electron donor show the oxidation and reduction properties as preferred. It further should be in the range that the color change properties and solubilities of electron acceptor and electron donor are as described above. The variation of the pH value of the composition may be made by selection of the type and the amount of any solvent or further ingredients including acidic substances (e.g. HCl or acetic acid), basic substances or the like.

The composition may also comprise a buffer. In the context of the present invention, all customary buffers are suitable, such as phosphate buffer, carbonate buffer, acetate buffer, formate buffer, citrate buffer, tris buffer, tris-(hydroxymethyl)-amino methane, glycylglycine buffer, glycine buffer, sodium phosphate buffer, sodium hydrogen phosphate buffer, sodium dihydrogen phosphate buffer, potassium phosphate buffer, potassium hydrogen phosphate buffer, potassium dihydrogen phosphate buffer or pyrophosphate buffer or mixtures thereof. Suitable are also sodium carbonate buffer, potassium carbonate buffer, sodium hydrogen carbonate buffer or potassium hydrogen carbonate buffer. Especially preferred as buffer are tris-(hydroxymethyl)-amino methane or glycylglycine.

The buffer concentration typically is in a range of about 0.01 to about 1.0 M or in a range of about 0.02 to about 0.5 M or in a range of about 0.03 to about 0.2 M with respect to the total composition.

The composition according to the present invention may optionally comprise further ingredients including e.g. a quinone or a disulfide compound. An example of a preferred quinone which can be used in the composition of the present invention is naphthoquinone. Preferred disulfide compounds which can be used in the composition of the present invention are oxidized lipoic acid, oxidized glutathione and/or cystine.

If a quinone is present, it is typically present in the inventive composition in a concentration of about 0.005 to about 0.5 mg/ml or from about 0.01 to about 0.05 mg/ml with respect to the total composition.

Lipoic acid may be present in the inventive composition for example in a concentration of about 0.05 to about 2.0 mg/ml or from about 0.1 to about 0.5 mg/ml with respect to the total composition.

One further embodiment of the described invention contains one or more auxiliary colorants. With an auxiliary colorant, the color of the inventive composition can be adjusted and the change of the color can be made better noticeable to the human eye, if desired. The auxiliary colorant has typically a different colour than the colour which might be produced by either the electron donor or electron acceptor component.

An appropriate auxiliary colorant can be a compound that does not change its color when the electrons are transferred from the electron donor to the electron acceptor. Instead, the auxiliary colorant provides the composition of the invention with a first color that will improve detection of the color change of the electron acceptor. For example, the auxiliary colorant can provide a background color to enhance the appearance of the change in the absorption profile.

For example, auxiliary colorants in the composition include but are not limited to: Patent Blue V, Patent Blue E 131, Erioglaucine, NEOZAPON blue 807 (commercially available from BASF, Ludwigshafen, Germany), methylene blue (commercially available from Hoechst), indigo carmine, indigo cartine (E 132), anthocyan (E 163); kurkumin (E 100), lactoflavin (E 101), Tatrazin (E 102), chinolin yellow (E 104), yellow orange S (E 110); cohenille (e 120), azorubin (E 122), amaranth (E 123), erythrosine (E 127), allura red (E 129) and ruby pigments (E 180) and mixtures or combinations thereof. Typically, amounts of auxiliary colorant of from about 5 ppm to about 1 wt.-% or from about 10 ppm to about 1000 ppm or from about 50 ppm to about 500 ppm, can be used if desired to prepare the compositions of the invention.

In another embodiment of the present invention the auxiliary colorant which can be used in the inventive composition can be a fluorescence dye, which emits fluorescence light at a wavelength which is absorbed by the reduced form of the electron acceptor but is not absorbed by any other constituent of the invented dental composition. In accordance to the invention the fluorescence light emitted typically has a wavelength in the range of about 380 nm to about 780 nm. A fluorescent dye can be for example a rhodamine, such as rhodamine 110.

A rhodamine dye may be present in the inventive composition for example in a concentration of about 0.005 to about 0.5 mg/ml or from about 0.01 to about 0.2 mg/ml with respect to the total composition.

The composition of the invention may further comprise one or more additives such as rheology modifiers, stabilizers, fillers and the like. It further can contain one or more additives to adjust the pH value of the composition. The rheology modifiers thicken the composition so that it remains on the surface of the tooth. Rheology modifiers may include, for example, inorganic materials such as fumed silica, quartz and glass having particle sizes of less than 1 µm. In particular materials having particle sizes in the range of 10 to 500 nm are desirable. Rheology modifiers can also include organic materials capable of thickening aqueous solutions, such as poly(meth)acrylic acid and its salts; polysaccharides such as gum arabic and cellulose derivatives such as hydroxyethylcelluloses, carboxymethyl celluloses; hydroxyethyl starches, xanthanates and alginates.

Generally, the compositions of the invention comprise additives in the amount of 0 wt.-% to about 30 wt.-% or from about 2 wt.-% to about 15 wt.-% or from about 3 wt.-% to about 13 wt.-% with respect to the weight of the whole composition.

Other, optional additives can include stabilizers as preservatives such as benzoic acids, benzoic acid esters usually in an amount of about 50 ppm to about 5 wt.-%.

Furthermore fillers such as glasses, quartz and Zirconica silicates, with a particle size of above about 0.6 µm can be added to the composition. These filler may be present in an amount of 0 wt.-% to about 70 wt.-% or from about 5 wt.-% to about 40 wt.-% or from about 10 wt.-% to about 40 wt.-%.

The dental composition according to the invention can be provided as a one compartment system. Thus, all components of the composition are contained in one solution. The solution can be packed in appropriate packaging devices, including e.g. a bottle having a volume of about 0.1 to about 10 ml volume, a unit-dose-packaging device of about 0.01 to about 1.0 ml volume or a bottle with integrated brush. Examples of such devices are described in more detail in U.S. Pat. No. 6,105,761 or U.S. Pat. No. 7,097,075, the content of which is herewith incorporated by reference.

The composition can further be provided as a two or more compartment system (kit of parts). Thus, a further embodiment of the invention is directed to a kit of parts comprising part A and part B, part A comprising the electron acceptor component and optionally a solvent and part B comprising the electron donor component and optionally a solvent, wherein the solvent and further optional components like the additives or auxiliary colorants described in the text of the present invention might be present either in part A or part B or in part A and part B.

The inventive composition comprises a solution of at least one electron acceptor component and at least one electron donor component wherein the electron acceptor component and the electron donor component are selected such that in the solution itself the electron donor can not transmit reduction equivalents to the electron acceptor.

This can be accomplished e.g. by providing a composition which is substantially free of components that enable or facilitate the electron transmission between the electron acceptor and the electron donor. Thus, componentes which are typically not present in the inventive composition are phenazine methosulfate (PMS) and/or Meldola's Blue (CAS: 7057-57-0).

Moreover, the inventive composition does typically not contain components like lactate dehydrogenase (LDH), sugar, pyruvate and mixtures of those, either.

Furthermore, the inventive composition does typically not contain NAD. E.g., adding NAD to the inventive composition would be detrimental in that the test does not function properly as desired.

The composition of the invention can be used in various fields including the dental and orthodontic area. In particular the inventive composition can be used for the site-directed intra-oral detection of bacteria e.g. on gum, enamel, dentin, root cement and dental restorations. The intra-oral applicability is a strong advantage of the composition as many other tests known from the art demand to collect a sample, e.g. of saliva, and to execute the detection of bacteria in vitro, in a separate vessel. Further, the composition and the use of this composition allow the site-directed detection of bacteria. By contrast many known tests only give hints to the presence of bacteria in the oral cavity but not in a particular region. The invention described herein in view of its intra-oral application can provide a site-directed detection. Thus, additional information about the location of the bacteria is available without spending additional time.

In a preferred embodiment, the inventive composition enables the practitioner to especially detect metabolic active bacteria in an excavated caries lesion.

By evaluating the intensity of the colour change obtained when applying the inventive composition to caries infected tooth tissue, it is also possible to link this signal to the numbers of bacteria present in on the caries infected tooth tissue.

A possible method of use of the dental composition comprises the steps of
a) providing a composition comprising a solution of at least one electron acceptor and at least one electron donor wherein the electron acceptor and the electron donor are selected that in the solution itself the electron donor can not transmit reduction equivalents to the electron acceptor and wherein the composition is substantially free of compounds that enable or facilitate the electron transmission between the electron acceptor and the electron donor,
b) applying said composition to dental tissue (including e.g. gum, tongue, enamel, dentin, root cement) and/or dental restorations, and
c) waiting for about 4 min or less (e.g. less than about 3 min or less than about 2 min or even less than about 1 min)

A color change of the composition within this time of about 4 minute or less typically indicates that bacteria are detected. If no color change occurs within this time frame, it is usually a hint for the absence of bacteria especially for the absence of certain kind of bacteria. For example it is typically a hint for the absence of bacteria which produce a reducing environment. After detecting the color change the dental practitioner has to make his diagnosis if the bacteria are caries causing or not. Thus, the composition, the use of this composition and a method of use of this composition only describe a detection of bacteria and no information is implemented if these bacteria are causing illness or not. The detection of the bacteria itself is intra-oral and site-directed.

One advantage of the inventive composition and its use is that it reduces the waiting time for the dental practitioner until he gets the results and based on the result can make a diagnosis or undertake further steps.

In addition to the detection of bacteria simply on the surface of dental tissue (e.g. a tooth surface), the composition and the use of this composition is further applicable for the detection of bacteria in excavated caries lesions. Moreover, the dental practitioner can use the composition according to the invention also to detect bacteria after an excavation treatment has been carried out.

Preferably, inventive dental composition may be used to detect bacteria intra-orally on certain specific sites. For example, the detection of bacteria in margins of fillings, in margins of crown and bridges, white spots, pits and fissures, plaque, dental calculus and/or initial caries is possible.

The present invention also relates to a method of producing a dental composition comprising the steps of preparing a solution by dissolving or adding at least one electron acceptor component and at least one electron donor component to a solvent wherein the electron acceptor component and the electron donor component are selected that in the solution itself the electron donor component can not transmit reduction equivalents to the electron acceptor component and wherein the composition does not contain added components enabling or facilitating the electron transmittal between said electron acceptor component and said electron donor component.

The composition of the above described invention can be used to manufacture a means or device for intra-oral detection of bacteria, especially for a means or device which can be used site-directed.

The following examples are given to illustrate only, but not limit, the scope of this invention. Unless otherwise indicated, all parts and percentages are by weight and all tests were conducted at ambient conditions (23° C.; 50% humidity and room pressure).

EXAMPLES

For all of the following examples, the compounds used are described as follows:

$Na_2$-NADH: reduced Nicotinamide adenine dinucleotide, disodium salt (available e.g. from Codexis or Applichem)

Acetyl-NADH: reduced 3-Acetylpyridine Adenine Dinucleotide (available e.g. from Speciality Assays)

Tris: Tris-(hydroxymethyl)-amino methane (available from e.g. Biomol or Applichem)

MTT: 3-(4,5-dimethylthiazol-2yl)-2,5-diphenyltetrazolium-bromide (available e.g. from Sigma Aldrich or Applichem)

PMS: Phenazine methosulphate (available e.g. from Applichem or Biolmol)

The other components used in the Examples can typically obtained from companies like Sigma Aldrich or Acros.

Example 1

Component 1

An aqueous solution was prepared by combining 100 ml of deionised water with 0.14 g β-Nicotinamide adenine dinucleotide, reduced disodium salt ($Na_2$-NADH) and 1.22 g Tris-(hydroxymethyl)-amino methane (Tris) adjusted to pH 11.4.

Component 2

A second solution was prepared of deionised water with 1.0 g 3-(4,5-dimethylthiazol-2yl)-2,5-diphenyltetrazolium-bromide (MTT) and 0.15 g KCl. This solution was then adjusted with HCl to a pH of 2.5. Deionised water was added until a total volume of 100 ml.

Example 1: Components 1 and 2 were mixed in a ratio of 3.6 to 1.

Example 1a

Component 1

An aqueous solution was prepared by combining 100 ml of deionised water with 1.4 g Acetyl-NADH and 1.22 g Tris-(hydroxymethyl)-amino methane (Tris) adjusted to pH 11.4.

Component 2

A second solution was prepared of deionised water with 1.0 g 3-(4,5-dimethylthiazol-2yl)-2,5-diphenyltetrazolium-bromide (MTT) and 0.15 g KCl. This solution was then adjusted with HCl to a pH of 2.5. Deionised water was added until a total volume of 100 ml.

Example 1a: Components 1 and 2 were mixed in a ratio of 3.6 to 1.

Into a carious lesion of an extracted human tooth 1-3 drops of Example 1 or Example 1a were given (depending on the size of the cavity). After 15 seconds, a blue-violet spot became visible formed by precipitated dye. Thus, clear distinct signals were observable indicating sites with elevated number of living bacteria.

Example 2

Component 1

An aqueous solution was prepared by combining 100 ml of deionised water with 0.14 g $Na_2$-NADH and 1.22 g Tris adjusted to pH 11.4.

Component 2

A solution was prepared of deionised water with 1.0 g 3-(4,5-dimethylthiazol-2yl)-2,5-diphenyltetrazolium-bromide (MTT) and 0.15 g KCl. The solution was then adjusted with HCl to a pH of 2.5. Deionised water was added until a total volume of 100 ml.

Component 3

A solution was prepared by combining 1 ml Poly(ethyleneglycol) 200 with 1.00 mg 3-methyl-naphthoquinone.

Mixture 1: 5 ml of Component 2 are mixed with 1 ml of Component 3.

Example 2: Mixture 1 and Component 1 were mixed in a ratio of 1.0 to 3.6.

Into a carious lesion of an extracted human tooth 1-3 drops of Example 2 were given (depending on the size of the cavity). After 15 seconds, a blue-violet spot became visible formed by precipitated dye. Thus, clear distinct signals were observable indicating sites with elevated number of living bacteria.

Example 3

Component 1

An aqueous solution was prepared by combining 1 ml of deionised water with 20 mg $Na_2$-NADH.

Component 2

2.00 mg Rhodamine was dissolved in 1.00 ml DMSO.

Component 3

13.214 g Glycylglycine was dissolved in deionised water. The solution was then adjusted with NaOH to a pH of 11.4. Deionised water was added until a total volume of 500 ml.

Component 4

A solution was prepared of deionised water with 1.0 g MTT and 0.15 g KCl. The solution was then adjusted with HCl to a pH of 2.5. Deionised water was added until a total volume of 100 ml.

Component 5

A solution was prepared by combining 1 ml Poly(ethyleneglycol) 200 with 1.00 mg 3-methyl-naphthoquinone.

Mixture 1:
5 ml of component 4 are mixed with 1 ml of component 5.
Example 3a: The mixing ratio for Component 1, 2, 3 and Mixture 1 was 4.0 to 1.0 to 17.0 to 6.0.

Into a carious lesion of an extracted human tooth 1-3 drops of Example 3 were given (depending on the size of the cavity). After 10 seconds, a blue-violet spot became visible formed by precipitated dye. Thus, clear distinct signals were observable indicating sites with elevated number of living bacteria.

Example 3a

Component 1

An aqueous solution was prepared by combining 1 ml of deionised water with 20 mg $Na_2$-NADH.

Component 2

2.00 mg Rhodamine was dissolved in 1.00 ml DMSO.

Component 3

13.214 g Glycylglycine was dissolved in deionised water. The solution was then adjusted with NaOH to a pH of 11.4. Deionised water was added until a total volume of 500 ml.

Component 4

A solution was prepared of deionised water with 1.0 g MTT and 0.15 g KCl. The solution was then adjusted with HCl to a pH of 2.5. Deionised water was added until a total volume of 100 ml.

Mixture 1:

A solution was prepared by combining 1 ml Poly(ethyleneglycol) 200 with 1.00 mg 3-methyl-naphthoquinone.

Mixture 1:

5 ml of component 3 are mixed with 1 ml of component 4.

Example 3: The mixing ratio for Component 1, 2, 3 and Mixture 1 was 4.0 to 1.0 to 17.0 to 6.0.

Into a carious lesion of an extracted human tooth 1-3 drops of Example 3 were given (depending on the size of the cavity). After 10 seconds, a blue-violet spot became visible formed by precipitated dye. Thus, clear distinct signals were observable indicating sites with elevated number of living bacteria.

Example 4

Component 1

An aqueous solution was prepared by combining 1 ml of deionised water with 20 mg $Na_2$-NADH.

Component 2

10.00 mg of oxidized lipoic acid was dissolved in 1.00 ml Ethanol.

Component 3

13.214 g Glycylglycine was dissolved in deionised water. The solution was then adjusted with NaOH to a pH of 11.4. Deionised water was added until a total volume of 500 ml.

Component 4

A solution was prepared in deionised water with 1.0 g MTT and 0.15 g KCl. The solution was then adjusted with HCl to a pH of 2.5. Deionised water was added until a total volume of 100 ml.

Example 4: The mixing ratio for Component 1, 2, 3 and 4 was 4.0 to 1.0 to 17.0 to 6.0.

Into a carious lesion of an extracted human tooth 1-3 drops of Example 4 were given (depending on the size of the cavity). After 15 seconds, a blue-violet spot became visible formed by precipitated dye. Thus, clear distinct signals were observable indicating sites with elevated number of living bacteria.

Example 5

Component 1

A solution was prepared of deionised water with 1.0 g MTT, 0.012 g PMS and 0.15 g KCl. The solution was then adjusted with HCl to a pH of 2.5. Deionised water was added until a total volume of 100 ml.

Component 2

13.214 g Glycylglycine was dissolved in deionised water. The solution was then adjusted with NaOH to a pH of 11.4. Deionised water was added until a total volume of 500 ml.

Example 5: The mixing ratio for Component 1 and 2 amounts 1.0 to 4.0.

Into a carious lesion of an extracted human tooth 1-3 drops of Example 5 were given (depending on the size of the cavity). After 120 seconds, a blue-violet spot became visible formed by precipitated dye. Thus, clear distinct signals were observable indicating sites with elevated number of living bacteria.

Example 6

A solution was prepared of deionised water with 1.0 g MTT, 0.012 g PMS and 0.15 g KCl. The solution was then adjusted with HCl to a pH of 2.5. Deionised water was added until a total volume of 100 ml.

Component 2

13.214 g Glycylglycine was dissolved in deionised water. The solution was then adjusted with NaOH to a pH of 11.4. Deionised water was added until a total volume of 500 ml.

Component 3

2.00 mg Rhodamine was dissolved in 1.00 ml DMSO.

Example 6: The mixing ratio for Component 1, 2 and 3 amounts 25.0 to 100.0 to 1.0.

Into a carious lesion of an extracted human tooth 1-3 drops of Example 6 were given (depending on the size of the cavity). After 120 seconds, a blue-violet spot became visible formed by precipitated dye. Thus, clear distinct signals were observable indicating sites with elevated number of living bacteria.

Example 7

Component 1

A solution was prepared of deionised water with 1.00 g MTT and 0.15 g KCl. The solution was then adjusted with HCl to a pH of 2.5. Deionised water was added until a total volume of 100 ml.

Component 2

An aqueous solution was prepared of deionised water with 1.22 g Tris. The solution was then adjusted with NaOH to a pH of 11.4. Deionised water was added until a total volume of 100 ml.

Example 7: Component 1 and Component 2 were mixed in a ratio of 1.0 to 3.6.

Into a carious lesion of an extracted human tooth 1-3 drops had been given (depending on the size of the cavity) of the Caries Indicator solution. After 300 seconds, a blue-violet spot became visible formed by precipitated dye. Thus, clear distinct signals were observable indicating sites with elevated number of living bacteria.

Example 8

Component 1

A solution was prepared of deionised water with 1.00 g MTT and 0.15 g KCl. The solution was then adjusted with HCl to a pH of 2.5. Deionised water was added until a total volume of 100 ml.

Component 2

A solution was prepared by combining 380 mg Meldola's blue with 100 ml of deionised water.
Mixture 1:
86.8 ml of Component 1 was mixed with 13.2 ml of Component 2.

Component 3

2.00 mg Rhodamine was dissolved in 1.00 ml DMSO.

Component 4

13.214 g Glycylglycine was dissolved in deionised water. The solution was then adjusted with NaOH to a pH of 11.4. Deionised water was added until a total volume of 500 ml.

Example 8: Mixture 1, Component 3 and 4 were mixed in a ratio of 25.0 to 1.0 to 100.0.

Into a carious lesion of an extracted human tooth 1-3 drops had been given (depending on the size of the cavity) of the Caries Indicator solution. After 300 seconds, a blue-violet spot became visible formed by precipitated dye. Thus, clear distinct signals were observable indicating sites with elevated number of living bacteria.

For all Examples 1 to 4 instead of $Na_2$-NADH different analogs of NADH and NADPH according to WO 98/33936 may be used. For example, in case of the analog 3-Acetylpyridine Adenine Dinucleotide in each of the Examples 1 to 4 an aqueous solution with an amount of 1.45 g Acetyl-NADH in 100 ml of deionised water and 0.12 mg Tris may be used. Other analogs of NADH and NADPH can be used also.

The results obtained are outlined in Table 1:

TABLE 1

| Ingredients | Ex 1 | Ex 1a | Ex 2 | Ex 3 | Ex 3a | Ex 4 | Ex 5 | Ex 6 | Ex 7 | Ex 8 |
| --- | --- | --- | --- | --- | --- | --- | --- | --- | --- | --- |
| MTT | X | X | X | X | X | X | X | X | X | X |
| NADH/NADH analogs | X | X | X | X | X | X | | | | |
| Quinone | | | | X | X | X | | | | |
| Rhodamine | | | | X | X | | | | X | X |
| oxidized lipoic acid | | | | | | | X | | | |
| PMS | | | | | | | | X | X | |
| Meldola's Blue | | | | | | | | | | X |
| time to the change of color [seconds] | 15 | 15 | 15 | 10 | 10 | 15 | 120 | 120 | 300 | 300 |

As can be seen from these examples the color change and the formation of a precipitation appeared much faster with solutions containing an electron acceptor and an electron donor according to the invention. For all solutions without electron donor the time to the change of the color is significantly longer. The same is true, if components like PMS or Meldola's Blue are present.

The invention claimed is:

1. A dental composition for detecting bacteria comprising
a solvent
at least one electron acceptor component and
at least one electron donor component,
the composition being free of components which enable or facilitate the electron transmission between the electron acceptor component and the electron donor component.

2. The composition according to claim 1, wherein the electron acceptor component and the electron donor component are selected such that in the solution itself the electron donor can not transmit reduction equivalents to the electron acceptor.

3. The dental composition according to claim 1, wherein the electron acceptor component has a color in its reduced state that is different from the color it has in its oxidized state and has at least in its reduced state a color in the range of about 380 nm to about 780 nm wave length of the spectrum.

4. The dental composition according to claim 1, wherein the electron acceptor component in its oxidized state has solubility of at least 0.01 wt.-% in the solution.

5. The dental composition according to claim 1, wherein the electron acceptor component in its reduced state precipitates from the solution.

6. The dental composition according to claim 1, containing the electron acceptor component in a concentration of about 0.01 to 80 wt.-% with respect to the total weight of the composition.

7. The dental composition according to claim 1, wherein the electron acceptor component is a tetrazolium compound or a tetrazolium derivative including 2,3,5-triphenyltetrazolium bromide, 2,3,5-triphenyltetrazolium chloride, 2,3,5-triphenyltetrazolium iodide, 3-(4,5-dimethyl)-2-thiazolyl(-2, 5-diphenyl-2H)-tetrazolium bromide (MTT), 2,5-diphenyl-3-(1-naphthyl)tetrazolium chloride (Tetrazolium Violet) and/or 2,2'-bipheny-4,4'-dihylbis-(3,5-diphenyl-2H-terazolium)-dichloride (Tetrazolpurpur), or combinations and mixtures thereof.

8. The dental composition according to claim 1 wherein the electron donor component is selected from the group consisting of reduced nicotinamide adenine dinucleotide, reduced nicotinamide adenine dinucleotidephosphate, reduced flavine adenine dinucleotide, reduced flavine mononucleotide or a derivative thereof and combinations or mixtures thereof.

9. The dental composition according to claim 1 containing the electron donor component in a concentration of about 0.01 to 80 wt.-% with respect to the total weight of the composition.

10. The dental composition according to claim 1, comprising a quinone, an oxidized glutathione, cystine and/or an oxidized lipoic acid.

11. The dental composition according to claim 1, comprising one or more additives selected from the group containing colorants being different from the electron acceptor or electron donor components, rheology modifiers, stabilizers, preservatives, fillers and combinations or mixtures thereof.

12. The dental composition according to claim 1, wherein the electron acceptor component is present in a concentration of about 1.0 to about 3.5 mg/ml.

13. The dental composition according to claim 1 having a pH value of from about 7 to about 10.

14. The dental composition according to claim 1, wherein the composition is free of components which enable or facilitate the electron transmission between the electron acceptor component and the electron donor component, such that the composition exhibits a color change when in the presence of bacteria.

15. The dental composition according to claim 14, wherein the color change includes at least one of:
- a change from one color to another distinct color,
- a change from colorless to a color,
- a change from a color to colorless, and
- a change from a color or colorless to fluorescence.

16. Kit of parts for detecting bacteria comprising part A and part B, part A comprising the electron acceptor component and part B comprising the electron donor component, wherein the solvent and optional additive(s) or optional auxiliary colorant(s) are present either in part A or part B or in part A and part B and wherein the electron acceptor component, the electron donor component, and the solvent are as described in claim 1.

17. A method for detecting bacteria, the method comprising:
- providing the dental composition of claim 1; and
- applying the dental composition intra-orally.

18. The method of claim 17, wherein applying the dental composition intra-orally includes applying the dental composition to at least one of gingiva, tongue, enamel, dentin, root cement, dental restorations, plaques, dental calculus, and a combination thereof.

19. The method of claim 17, further comprising detecting bacteria, if present, intra-orally with site-directed localization.

20. The method of claim 17, further comprising detecting whether a color change occurs in the dental composition in 4 min. or less after applying the dental composition intra-orally.

* * * * *

UNITED STATES PATENT AND TRADEMARK OFFICE
CERTIFICATE OF CORRECTION

Page 1 of 2

PATENT NO. : 8,834,851 B2
APPLICATION NO. : 12/677377
DATED : September 16, 2014
INVENTOR(S) : Haeberlein et al.

It is certified that error appears in the above-identified patent and that said Letters Patent is hereby corrected as shown below:

Title Page

Column 2 (Abstract)
Line 8-9, Delete "inter-oral" and insert -- intra-oral --, therefor.

Column 2 (Other Publications)
Line 5, Delete "Caivty" and insert -- Cavity --, therefor.

In the Specification

Column 2
Line 22, Delete "Pyruvat," and insert -- Pyruvate, --, therefor.
Line 38, Delete "water" and insert -- water. --, therefor.
Line 43, Delete "dinucleotid," and insert -- dinucleotide, --, therefor.

Column 6
Line 61, Delete "benzothiaolyl" and insert -- benzothiazolyl --, therefor.
Line 62, Delete "benzothiaolyl" and insert -- benzothiazolyl --, therefor.

Column 7
Line 24, Delete "dimethylpheny" and insert -- dimethylphenyl --, therefor.
Line 26, Delete "dipheny" and insert -- diphenyl --, therefor.
Line 32, Delete "(-2,5-diphenyl" and insert -- (2,5-diphenyl --, therefor.
Line 33, Delete "(-2,5-diphenyl" and insert -- (2,5-diphenyl --, therefor.
Line 52, Delete "bipheny" and insert -- biphenyl --, therefor.
Line 53, Delete "dichlorid" and insert -- dichloride --, therefor.
Line 54, Delete "thiocarbamyl" and insert -- thiocarbamoyl --, therefor.
Line 62, Delete "bipheny" and insert -- biphenyl --, therefor.

Signed and Sealed this
Twenty-fourth Day of February, 2015

Michelle K. Lee
*Deputy Director of the United States Patent and Trademark Office*

CERTIFICATE OF CORRECTION (continued)
U.S. Pat. No. 8,834,851 B2

Column 8
Line 58, Delete "ketons" and insert -- ketones --, therefor.

Column 9
Line 16, Delete "furane," and insert -- furan, --, therefor.
Line 16, Delete "methyethyl" and insert -- methylethyl --, therefor.
Line 17, Delete "methylen" and insert -- methylene --, therefor.

Column 10
Line 22, Delete "kurkumin" and insert -- curcumin --, therefor.
Line 23, Delete "Tatrazin" and insert -- Tatrazine --, therefor.
Line 24, Delete "cohenille" and insert -- cochenille --, therefor.
Line 24, Delete "(e 120)" and insert -- (E120) --, therefor.

Column 11
Line 1, Delete "Zirconica" and insert -- Zirconia --, therefor.

Column 12
Line 2, Delete "in on" and insert -- in --, therefor.
Line 17, Delete "1 min)" and insert -- 1 min). --, therefor.

In the Claims

Column 18
Line 33-34, In Claim 7, delete "(-2,5-diphenyl" and insert -- (2,5-diphenyl --, therefor.
Line 36, In Claim 7, delete "bipheny" and insert -- biphenyl --, therefor.